United States Patent
Erickson et al.

(10) Patent No.: US 12,213,894 B2
(45) Date of Patent: Feb. 4, 2025

(54) QUANTITATIVE ASSESSMENT OF ORBIT SOFT TISSUE RESTRICTION

(71) Applicant: The Board of Trustees of the Leland Stanford Junior University, Stanford, CA (US)

(72) Inventors: Benjamin Peter Erickson, Palo Alto, CA (US); Henry Bair, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 656 days.

(21) Appl. No.: 17/613,236

(22) PCT Filed: Jun. 4, 2020

(86) PCT No.: PCT/US2020/036106
§ 371 (c)(1),
(2) Date: Nov. 22, 2021

(87) PCT Pub. No.: WO2020/247617
PCT Pub. Date: Dec. 10, 2020

(65) Prior Publication Data
US 2022/0211521 A1 Jul. 7, 2022

Related U.S. Application Data

(60) Provisional application No. 62/858,070, filed on Jun. 6, 2019.

(51) Int. Cl.
*A61F 2/46* (2006.01)
*A61F 2/28* (2006.01)

(52) U.S. Cl.
CPC .... *A61F 2/4657* (2013.01); *A61F 2002/2878* (2013.01); *A61F 2002/4666* (2013.01)

(58) Field of Classification Search
CPC ............ A61F 2/4657; A61F 2002/2878; A61F 2002/4666; A61B 5/103; A61B 5/6821
See application file for complete search history.

(56) References Cited

U.S. PATENT DOCUMENTS

| | | | |
|---|---|---|---|
| 6,595,641 B1 * | 7/2003 | Braeuning | A61B 3/113 351/208 |
| 2015/0335479 A1 * | 11/2015 | Shibata | A61F 9/009 606/4 |

* cited by examiner

*Primary Examiner* — James C. Jones
(74) *Attorney, Agent, or Firm* — LUMEN PATENT FIRM

(57) ABSTRACT

A portable device, method and system are provided for automated, quantitative assessment of orbital compliance and soft tissue restriction with emphasis on applicability to orbital trauma and fracture management is provided.

7 Claims, 3 Drawing Sheets

QUANTITATIVE ASSESSMENT OF ORBIT SOFT TISSUE RESTRICTION

FIELD OF THE INVENTION

This invention relates to devices, methods and systems for soft tissue restriction analysis. In particular, the invention relates to orbital soft tissue restriction assessment.

BACKGROUND OF THE INVENTION

There is extensive focus on recapitulating the three-dimensional (3D) configuration and volume of the bony orbit (eye socket) following traumatic fractures, as well as the substantial progress in the form of mirroring/transposition of the uninjured side, 3D customization and printing of implants, and use of intraoperative navigation systems to guide implant localization and fixation.

Many of the most significant complications of orbital fractures and their surgical repair, however, relate not to appropriate volumetric restoration, but rather to persistent or iatrogenic soft tissue entrapment, which can lead to persistent pain and/or disabling double vision for the affected patient. In point of fact, as custom implant contours become more sophisticated, they also become more challenging to implant successfully without soft tissue dragging and potential restriction.

While there are highly-evolved solutions for the restoration of bony contour, the art currently lacks quantitative means of assessing soft tissue entrapment pre-, intra-, and to guide clinical decision making. 'Forced duction' testing involves using fine forceps to grasp the ocular surface with millimeter precision adjacent to the corneoscleral limbus, and manipulating the eye to assess range of motion and any movement restriction due to soft tissue entrapment.

While data from this activity theoretically could be represented graphically on an X-Y axis for each cardinal direction of eye movement, forced ductions as currently practiced results in a binary designation of 'positive' or 'negative', as determined by 'expert feel'. Since the current gold standard is clinical intuition of the individual surgeon, there are significant concerns with regard to inter- and intra-rater variability, and there are no normative population data to which measurements can be compared. Postoperatively, when eye motility outcomes are sub-optimal, it becomes very challenging to determine whether the issue is persistent/iatrogenic soft tissue entrapment that requires reoperation or merely traumatic myopathy that will recover in time with conservative management.

The majority of orbital fractures are also repaired by surgeons without ophthalmic training, not all of whom have the same degree of comfort with globe manipulation by means of precision grasping of the conjunctiva-Tenon's fusion plane adjacent to the corneoscleral limbus. Without knowledge of these anatomical landmarks and competency in this method of manipulation, the chance of obtaining clinically useful data goes down, while the risk of corneal injury and/or conjunctival laceration goes up. Thus, the current 'gold standard' for assessing range of motion and soft tissue resistance is not only limited in its clinical efficacy, but is furthermore not easily applied by all surgeons.

With these factors in mind, there is a compelling need for a reproducible and quantitative method and device for determining orbital soft tissue entrapment that does not rely on precision grasping of the globe and can be used to guide decision making pre-, intra-, and postoperatively.

Additionally, there are a broad variety of restrictive and myopathic orbital pathologies for which precise quantification of soft tissue parameters could improve the precision of interventions aimed at restoring coordinated ocular motility and alleviating double vision. The goal is therefore to develop a platform and descriptive system for automated mapping of orbital compliance and force generation applicable to this range of clinical problems.

SUMMARY OF THE INVENTION

The present invention provides a device for quantitative assessment of orbital soft tissue restriction. The device distinguishes a motion-generation unit having a vertical motor and rotational motor stacked with a translation motor (also referred to as vertical stage, rotational stage, and translational stage, respectively). A primary resistance measurement sensor (primary load cell) is configured in between the motion-generation unit and a suction cup. Additional (secondary) resistance measurement sensors are present in conjunction with the vertical and rotational motors (vertical load cell and torsional load cell, respectively). The suction cup is suitable to fit a front part of an eye. The device further distinguishes a controller for controlling the rotational motor and the translation motor in the motion-generation unit to generate and control a motion path of the suction cup and therewith motion of the eye. A data collection unit collect data from the resistance measurement sensor during the execution of the motion path of the suction cup. The collected data provides insight in an orbital range of motion or an orbital soft tissue resistance as a function of the motion path of the suction cup. The data collection unit can be an integral part of the device or communicatively connected to the device.

In one example, the device is a handheld device. However, the device could have a mounting device to be mounted to a bony structure (e.g. head) of a person from which the data is collected or mounted to an external device or surgical table.

Further provided is a method for quantitative assessment of orbital soft tissue restriction. The method includes the steps of placing a suction cup suitable to fit a front part of an eye is placed, having a motion-generation unit comprising a rotational motor and a translation motor, controlling the rotational motor and the translation motor to generate and control a motion path of a suction cup and therewith a motion of the eye, measuring resistance of the motion path of the suction cup and therewith of the eye with a resistance measurement sensor configured in between the motion-generation unit and the suction cup, and collecting data from the resistance measurement sensor during the execution of the motion path of the suction cup, wherein the collected data provides insight in an orbital range of motion or an orbital soft tissue resistance as a function of the motion path of the suction cup.

When mounted to an external device or surgical table, the vertical motor and accompanying resistance measurement sensor provide a means of neutralizing the pressure applied by the device on the orbital tissues to standardize soft tissue measurement parameters. Standardized motor driven vertical movement transiently depressing the globe into the orbital tissues also measures a dimension of soft tissue compliance that may be applied to reconstructive interventions.

With the suction cup affixed to the surface of the eye, but freely rotating at the device interface, the rotational motor stage provides a way of rotating the translational motor stage through a 360-degree scan pattern. When the suction cup-device interface is fixed, the force measurement sensor accompanying the rotational motor stage permits measurement of torsional soft tissue resistance applicable to disorders of eye cyclo-rotation, such as oblique muscle pathology.

Embodiments of the invention are useful in the management of a broad range of restrictive, neuropathic and myopathic processes such as thyroid orbitopathy, chronic cranial nerve palsy, and congenital strabismus syndromes. Specifically, embodiments are useful in:

Orbital fractures (especially complex repairs in conjunction with large and/or custom implants).
Orbital reconstruction following skull base or sinus surgery.
Thyroid eye disease.
Congenital myopathy and fibrosis syndromes.
3rd nerve palsy and other large angle strabismus syndromes.

DETAILED DESCRIPTION

Figure 1:
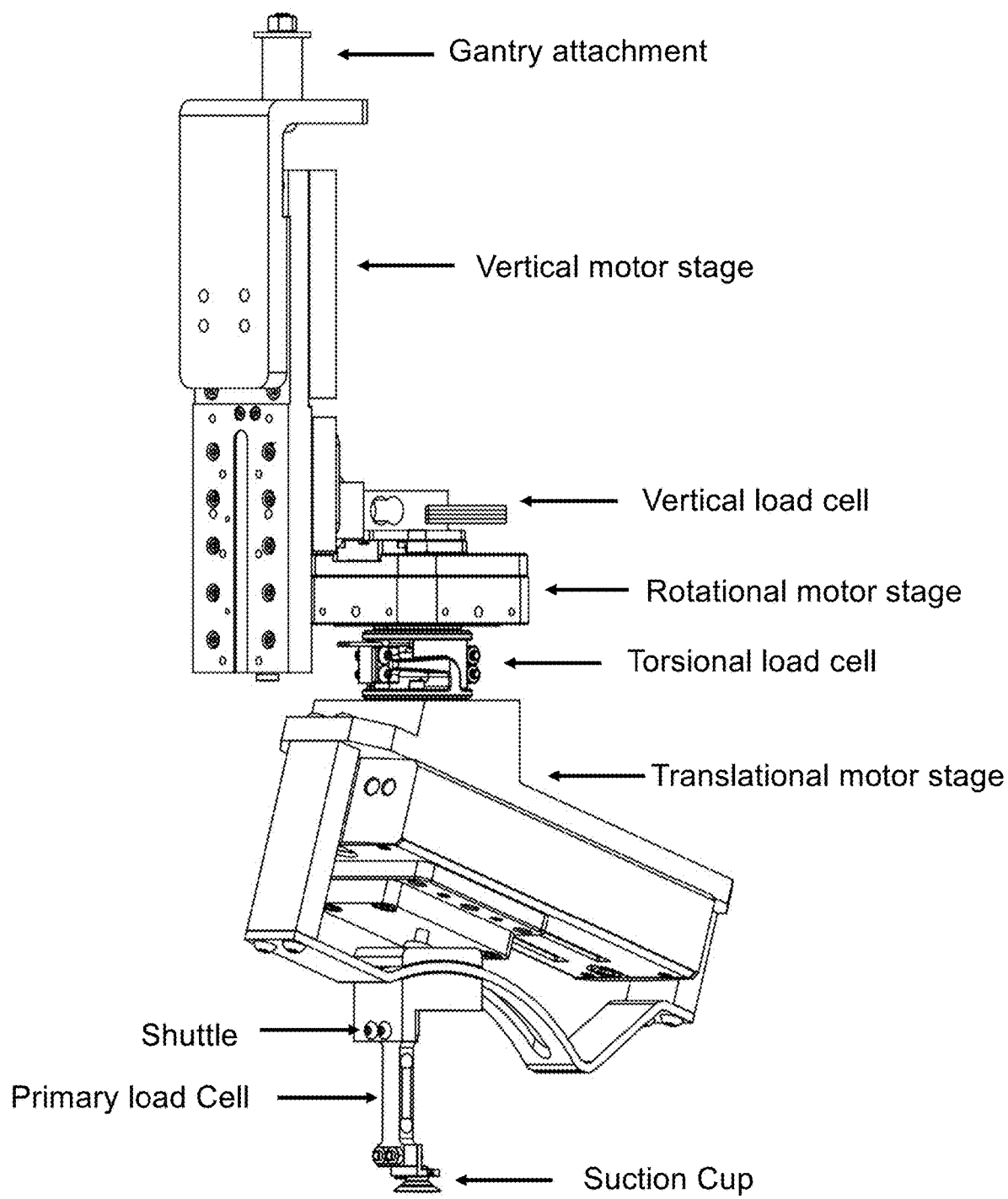
FIGS. 1-2 show different aspects of the device according to an exemplary embodiment of the invention.
Figure 2:
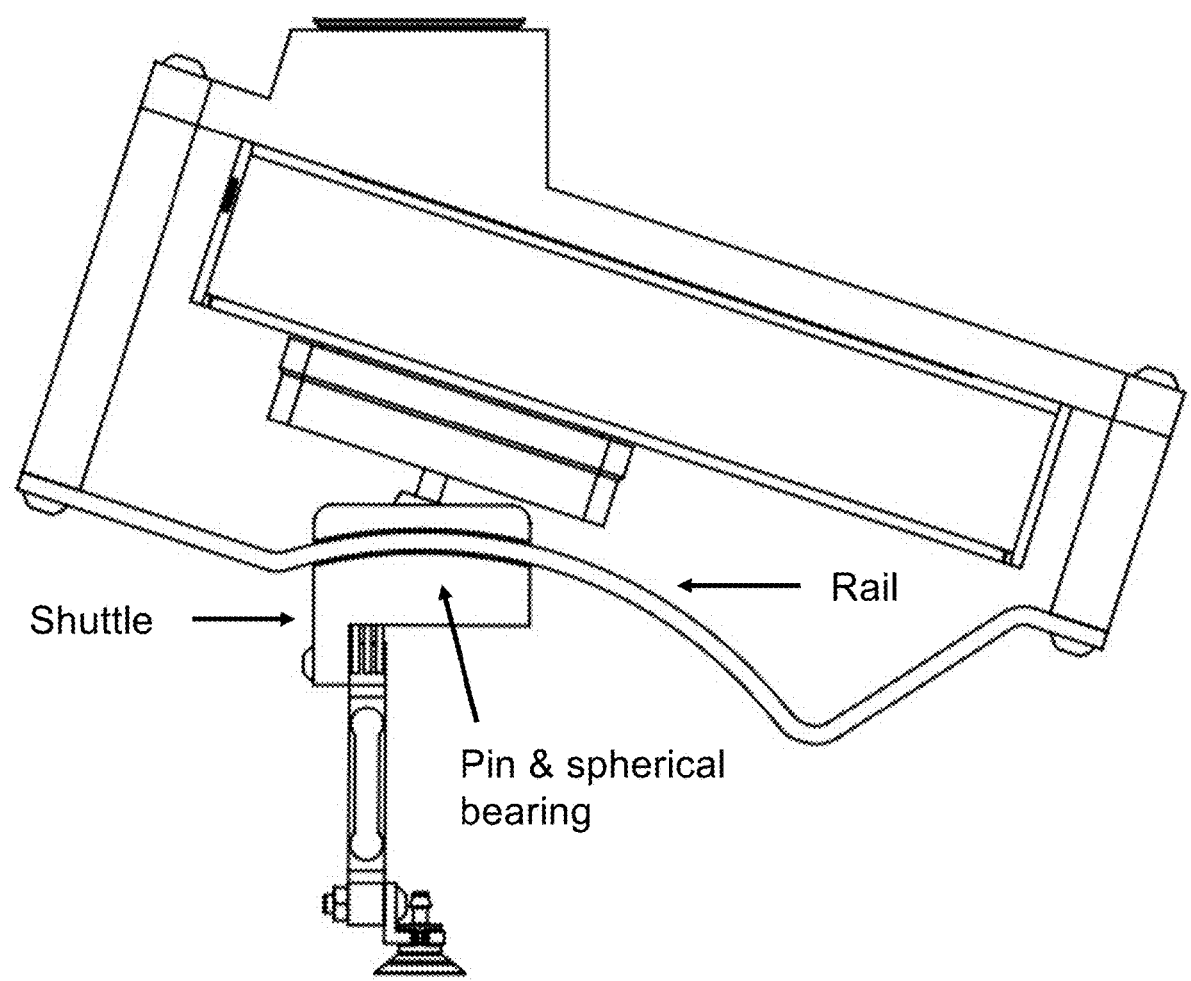
Figure 3:
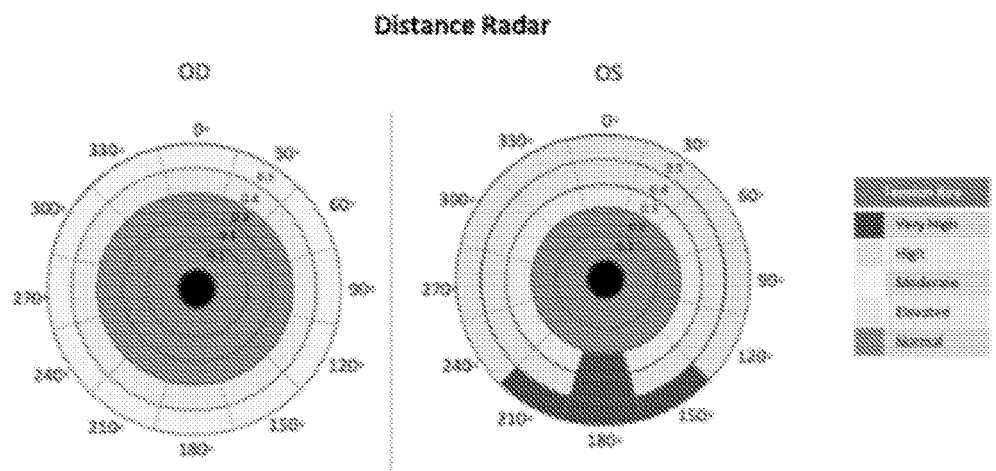
FIG. 3 shows an example of a soft tissue and orbital range of motion analysis report based on the data obtained from the device according to an exemplary embodiment of the invention.
Figure 3:
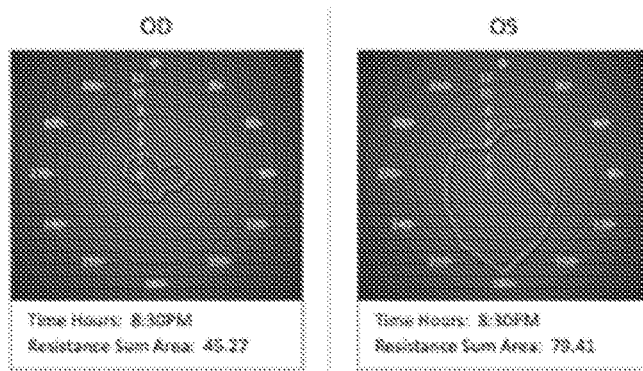
Figure 3:
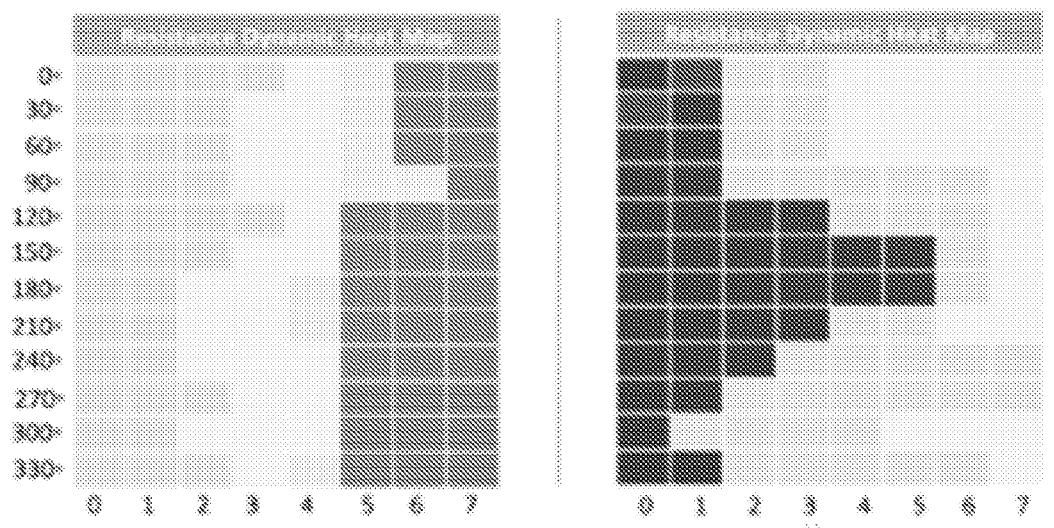

Provided herein is a device that can collect quantitative data regarding soft tissue resistance and range of motion, not only in the classic cardinal directions (infra/supraduction and ab/adduction), but in any clock hour deemed clinically helpful. This includes the ability to measure resistance to retropulsion of the globe into the orbital soft tissues, as well to measure torsional resistance to cyclo-rotation.

In one embodiment, the device uses stacked vertical, rotational and translational piezoelectric motor stages, that are mounted to a locking gantry. Piezoelectric motors use the expansion of specific crystalline structures in response to graded electrical input to create precise motion. A linear stage with a controller unit, mounted on a rotational stage, is used to produce precise and quantifiable motion, thus eliminating the subjective influence of the surgeon performing manual forced ductions. Non-contact optical encoders within the device are used to measure the position of the platform via a closed loop system, so that the device always 'knows' where the manipulated tissue interface is with micrometer precision. The function of the piezoelectric motors could also be accomplished using servo motors with similar control systems.

The quantifiable linear motion is then converted into standardized radial motion via a pin that interfaces between the linear piezo stage and a 3D printed and machined radial translation rail and shuttle. To generate an appropriate vector for reproducible globe manipulation, the radius of curvature for the translation rail and stage were set as the cumulative height of the stage and additional device elements (e.g. an embedded load cell and suction coupler) added together with the radius/center of rotation of an average globe (12 mm).

A miniature parallel beam load cell containing strain gauges in Wheatstone bridge configuration is embedded into the radial translation platform and anchored via M2.5 bolts. The load cell is spliced to interface wires, wrapped with electrical heat shrink tubing, and connected to a load cell amplifier/microcontroller. The opposite end of the load cell is secured to a machined suction mount bracket via a M2.5 bolt/nut combination. The load cell measures the resistance to excursion tangent to the curvilinear range of motion path, permitting construction of a force-versus-distance travelled graph for each clock hour vector.

Unlike currently performed forced ductions, which require precision grasping of the ocular surface with fine forceps, the ocular surface interface of the device provided herein is suction based. In one example, a 15 mm silicone suction cup is bonded with epoxy resin to a modified 18-gauge needle connected via butterfly needle tubing to a 3 mm syringe modified with a compression spring around the plunger. This device can be filled with balanced salt solution, hyaluronic acid gel, or air to couple reliably and a-traumatically with the ocular surface. The strength of suction can be set depending on how much the compression spring is depressed, and subsequent data collection can be used to determine and pre-set optimal suction pressures in the system to avoid slippage on the one hand and tissue trauma on the other. Other iterations of the design could have the suction interface as a corneal shield placed at the beginning of the case for globe protection, which is then connected to the force and distance sensing unit at the appropriate time during surgical manipulation.

The piezoelectric controller is programmed to stop translational/radial motion when resistance on the load cell exceeds a critical threshold, to prevent over-extension of the system, breach of the suction force coupling the device to the globe, or damage to the ocular surface.

A free axis of rotation exists at the suction mount bracket so that the device can be turned a pre-determined number of degrees by the rotational stage before repeating the measurement protocol without detaching the suction interface. This mapping of resistance-versus-excursion in multiple clock hours can be used to produce an orbital 'heat map' with 3D graphic output that precisely quantifies where within the orbit soft tissue entrapment or resistance exists in a fashion similar to optic coherence tomography (OCT) mapping for retinal nerve fiber layer (RNFL) mapping for glaucoma and other intraocular pathologies. Particularly when inserting an orbital implant with a complex 3D contour, this 'heat map' could be very helpful in terms of assessing where the inserted implant may be dragging or impinging upon previously mobilized soft tissues. In another embodiment, this data also can be compared against a normative population database and/or data from the patient's uninjured side. It could also be used to assess the disease course of restrictive myopathies such as thyroid eye disease (TED) or congenital fibrosis.

An adaptation, essentially running the device in reverse such that the piezoelectric elements translate force into graded electrical output, would permit the device to be used to measure muscle force generation in awake patients and to produce a similar map describing force and excursion in the cardinal gaze directions and in each clock hour. This could then be used as a platform to assess recovery from muscle trauma or other types of myopathy, thereby better prognosticating return to function, and even conceivably to help program muscle prostheses to treat challenging forms of neuropathic and myopathic strabismus, such as 3rd nerve palsy.

The primary resistance measurement load cell is configured in between the translational piezoelectric platform and the suction cup. Additional dual beam load cells are present in conjunction with the vertical and rotational piezoelectric motors. Application of non-standardized vertical force to the orbital tissues can affect the measurements obtained in the aforementioned 360-degree resistance-versus-excursion heat map. When mounted to an external device or surgical table, the vertical piezo motor and accompanying load cell therefore provide a means of neutralizing the pressure applied by the device on the orbital tissues, similar to the 'tare' function on an electronic scale. The device may therefore be brought into gross position, the gantry locked, and the suction interface secured to the ocular surface. The vertical motor stage and accompanying load cell may then be used to fine tune device positioning, neutralizing the downward force applied to the ocular surface prior to data acquisition.

Standardized motor driven vertical movement also provides a way of quantitatively measuring a clinical parameter known as 'resistance to retropulsion'. In cicatricial orbital pathology, the ease of manually depressing the eye into the surrounding soft tissues is recorded as a factor considered relevant to monitoring disease progression and assessing response to therapeutic outcomes. However, similar to 'forced duction' testing, neither the degree of resistance nor the amount of deflection over which this resistance is measured are currently standardized or quantifiable in clinical practice. The vertical piezo motor and accompanying load cell sensor may be programmed to provide an automated 'resistance to retropulsion' measurement.

With the suction cup affixed to the surface of the eye, but freely rotating at the primary dual beam load cell interface, the rotational piezoelectric stage provides a means of rotating the translational piezoelectric motor stage through a 360-degree scan pattern for acquisition of resistance-versus-excursion data in each clock hour. When the suction cup-device interface is held in a fixed position via a locking mechanism, however, the torsional load cell accompanying the rotational piezo motor stage permits measurement of soft tissue resistance to rotational movement. Rotation of the globe in a clockwise versus counterclockwise direction will produce a measurement corresponding with 'in-cyclo-torsion' or 'ex-cyclo-torsion' depending on whether movement is applied to a right or left eye. Similar to the automated 'forced duction' excursion, the number of degrees that the globe is rotated in either direction has a programmed limit when resistance on the load cell exceeds a critical threshold, to prevent over-extension of the system, breach of the suction force coupling the device to the globe, or damage to the ocular surface. These measurements are applicable to surgical management of disorders of eye cyclo-rotation, such as 4$^{th}$ nerve palsy, where the degree of muscle plication is currently guided by expert feel.

What is claimed is:

1. A device for quantitative assessment of orbital soft tissue restriction, comprising:
    (a) a motion-generation unit, wherein the motion-generation unit comprises stacked vertical, rotational and translation motor stages;
    (b) a suction cup suitable to fit a front part of an eye;
    (c) a primary resistance measurement sensor, wherein the resistance measurement sensor is configured in between the motion-generation unit and the suction cup;
    (d) secondary resistance measurement sensors, wherein the secondary resistance measurement sensors are linked to the vertical and rotational motor stages;
    (e) a controller controlling the rotational motor stage and the translation motor stage in the motion-generation unit to generate and control a motion path of the suction cup and therewith a motion of the eye;
    (f) a controller controlling a vertical excursion of the device and neutralizing force applied to globe and orbital soft tissues of the eye; and
    (g) a data collection unit to collect data from the resistance measurement sensors during the execution of the motion path of the suction cup, wherein the collected data provides insight in an orbital range of motion or an orbital soft tissue resistance as a function of the motion path of the suction cup.

2. The device as set forth in claim 1, wherein the device is a handheld device.

3. The device as set forth in claim 1, wherein the device has a mounting device to be mounted to a bony structure of a person from which the data is collected.

4. The device as set forth in claim 3, wherein the bony structure is a person's head.

5. The device as set forth in claim 1, wherein the device is mounted to an external device.

6. The device as set forth in claim 5, wherein the external device is a surgical table.

7. A method for quantitative assessment of orbital soft tissue restriction, comprising:
    (a) placing a suction cup suitable to fit a front part of an eye;
    (b) having a motion-generation unit comprising a vertical motor, a rotational motor and a translation motor;
    (c) controlling the vertical motor, the rotational motor and the translation motor to generate and control a motion path of a suction cup and therewith a motion of the eye;
    (d) measuring resistance of the motion path of the suction cup and therewith of the eye with a resistance measurement sensor configured in between the motion-generation unit and the suction cup; and
    (e) collecting data from the resistance measurement sensor during the execution of the motion path of the suction cup, wherein the collected data provides insight in an orbital range of motion or an orbital soft tissue resistance as a function of the motion path of the suction cup.

* * * * *